United States Patent [19]

Benzaria

[11] Patent Number: 5,254,666
[45] Date of Patent: Oct. 19, 1993

[54] PROCESS FOR PRODUCTION OF ALKALINE OR ALKALINE-EARTH METAL TEREPHTHALATE OR OF TEREPHTHALIC ACID, OF HIGH PURITY, FROM POLYOL POLYTEREPHTHALATE AND IN PARTICULAR FROM WASTE OF AN ETHYLENE GYLCOL POLYTEREPHTHALATE

[75] Inventor: Jacques Benzaria, Chambly, France

[73] Assignee: Institut Francais du Petrole, Rueil Malmaison, France

[21] Appl. No.: 827,050

[22] Filed: Jan. 29, 1992

[30] Foreign Application Priority Data

Jan. 30, 1991 [FR] France .................. 91 01025

[51] Int. Cl.$^5$ .................. C08G 63/02; C07C 63/14
[52] U.S. Cl. .................. 528/272; 562/480; 562/485
[58] Field of Search .................. 528/272; 562/480, 485

[56] References Cited

U.S. PATENT DOCUMENTS

| 610,135 | 10/1948 | Heath et al. | 562/485 |
| 3,873,609 | 3/1975 | Wu et al. | 562/481 |
| 3,952,053 | 4/1976 | Brown, Jr. et al. | 562/483 |
| 3,953,502 | 4/1976 | Fassell et al. | 562/485 |
| 4,355,175 | 10/1982 | Pusztaszeri | 562/485 |

FOREIGN PATENT DOCUMENTS 0134866 4/1947 Australia .

*Primary Examiner*—John Kight, III
*Assistant Examiner*—T. Mosley
*Attorney, Agent, or Firm*—Millen, White, Zelano & Branigan

[57] ABSTRACT

Production of alkali metal or alkaline-earth metal terephthalate by reaction of an alkali metal or alkaline-earth metal hydroxide with a polyol polyterephthalate, and optional conversion of the terephthalate into terephthalic acid.

The reaction is performed without addition of water or in the presence of an amount of water representing at most, by weight, the amount of polyterephthalate.

The invention is useful for the treatment of polyol polyterephthalate waste.

14 Claims, No Drawings

PROCESS FOR PRODUCTION OF ALKALINE OR ALKALINE-EARTH METAL TEREPHTHALATE OR OF TEREPHTHALIC ACID, OF HIGH PURITY, FROM POLYOL POLYTEREPHTHALATE AND IN PARTICULAR FROM WASTE OF AN ETHYLENE GYLCOL POLYTEREPHTHALATE

BACKGROUND OF THE INVENTION

The invention relates to the production of terephthalates of alkaline or alkaline-earth metals from polyol polyterephthalate and in particular from glycol polyterephthalate (P.E.T.).

The difficulties of recycling P.E.T.-type polyesters are due mainly to the coloring and to the foreign substances that are found mixed, with these products, and to the difficulty of elimination of the water marks in the recycled product.

One of the best forms of recovery is a depolymerization and recovery from terephthalic acid and glycol in the form of raw materials that can result in new polyesters of the same purity as the products produced from new raw materials.

The breakdown of the P.E.T. and of the polyesters having terephthalic acid as a dibasic acid is described in the prior art as being performed in an aqueous soda solution containing 3 to 20% by weight of soda, at a pressure of 1.38 to 2.07 MPa (200 to 300 PSI) and at a temperature between 180° and 320° C., preferably between 210° and 250° C. (U.S. Pat. No. 3,317,519).

In batch installations, this process results in a considerable use of energy, and requires a material that must withstand the pressure.

The hydrolysis periods are long, from 3 to 5 hours, and the amount of soda used is on the order of 1.5 in comparison with the theory.

According to another proposal (GB-A-822,834), it is desired to obtain salting out of the terephthalic acid salt either by operating at 100° C. with a relatively dilute aqueous solution of sodium hydroxide or by operating in the presence of an alcohol. The presence of an alcohol in the present invention is not necessary and is even considered detrimental.

SUMMARY OF THE INVENTION

The process of the invention eliminates these deficiencies of the prior art by proposing a process which can be performed more quickly at a lower temperature, under a lower pressure and particularly under normal pressure, and under conditions which make possible continuous operation and obtaining of terephthalic acid of a quality suitable for its use in polymerization. The consumption of energy is therefore lower, and it is possible to use a piece of equipment that is not very expensive since it does not need to withstand high pressure.

Another advantage of the process is selectivity. Thus, when certain other polymers or polycondensates are present in the starting charge, they can remain unaffected by the treatment and therefore be easily separated at the end of the reaction. This is the case, for example, of polyethylene, polypropylene and certain natural fibers, for example cellulose in the form of cotton fibers or paper (paper labels, for example).

According to a particular embodiment, a simple treatment makes it possible to eliminate the dyes present in the starting charge.

The process of the invention involves reacting a polyol polyterephthalate with an alkali metal or alkaline-earth metal hydroxide in the absence of water or in the presence of water in an amount at most equal by weight to that of the alkali metal or alkaline-earth metal hydroxide.

The operation is performed advantageously above 120° C. The pressure is advantageously equal to normal atmospheric pressure or close to it. There is no compelling advantage to operating under pressure, the reaction speed already being elevated at normal pressure.

The reaction is generally fast, most often between 1 and 60 minutes, for example 15, minutes.

The alkali metal or alkaline-earth metal hydroxide can be used in stoichiometric proportion in relation to the polyterephthalate, i.e., in the amount necessary to produce the desired salt. Although it is possible to produce the monoacid terephthalate of the selected metal, it is preferred to produce the terephthalate entirely salified, which requires two alkali metal atoms or one alkaline-earth metal atom per terephthalic group present. It is also possible to perform the operation with an excess or a deficiency of hydroxide, for example an excess or a deficiency up to 50% or more. For example, it is possible to perform the operation with 50 to 300% of the theoretical amount of hydroxide, preferably 50 to 150%.

By way of example, it is possible to use the hydroxides of sodium, potassium, calcium, barium or magnesium, or the oxides of the same metals, by hydrating them.

It is possible to perform the operation without water, for example by heating in an extruder.

At the end of the reaction, if the amount of water is not sufficient to dissolve the terephthalate, when the latter is soluble in water, the water necessary to assure this dissolving is effectively added. This will be the case, for example, for the sodium and potassium terephthalates. The terephthalates of alkaline-earth metals, generally not very soluble, are separated by precipitation.

If it is desired to eliminate the polyol released by the reaction, it is possible to proceed by salting out of the filtration liquid by increasing the ionic force of the solution, for example by addition of sodium chloride. The polyol thus separated can be purified by distillation or by any other known method.

If other nonreactive polymers are present in the charge, they are easily separated from the aqueous solution of alkali metal or alkaline metal terephthalate because of their insolubility in this solution. This is the case, for example, of the empty used plastic bottles, often having a polyethylene base, including the old labels of these bottles.

When higher purity and complete bleaching of the product is desired, and particularly when it is desired to obtain a terephthalic acid of polymerizable quality, the invention proposes a process for bleaching this solution by extraction by means of an alcohol that is not very soluble in water, having at least 3 carbon atoms per molecule, and preferably with an alcohol in C3 to C8 or better in C4 to C6. N-butanol is preferred at a temperature between 40° and 80° C.

The operation is performed preferably at a temperature between 40° and 80° C., and more generally between 10° and 150° C. The pressure can be, for example, from 0.1 to 1 MPa. The amount of alcohol represents effectively 5 to 100% of the volume of the solution treated.

It is thus possible to obtain a bleached aqueous solution of alkali metal or alkaline earth metal terephthalate.

When the salt obtained from terephthalic acid is insoluble, which is the case, for example, of calcium terephthalate, it is also possible to purify it more by extraction by means of an alcohol of 1-8 carbon atoms, preferably in an amount representing 5 to 100% of the weight of this salt.

If it is desired to obtain terephthalic acid itself, it is possible to acidify the solution with a sulfuric, phosphoric, or hydrochloric acid or an organic acid, with a pH of 1 to 4 and preferably of 2.5 to 3 suitable for this operation. The insoluble terephthalic acid is then obtained in high purity, after washing to eliminate the salt products.

EXAMPLES

Example 1

1178 kg of support of X-ray films of glycol polyterephthalate, cleared of silver and of gelatin, are mixed cold with 500 kg of soda at 100° C. with agitation, then 100 liters of water are introduced into the mixture. The mixture is distributed in a screw exchanger where the temperature is 160° C., the introduction speed being calculated so that the temperature of 160° C. is reached at mid-course. The product is collected in an agitated vessel in which the amount of water necessary to arrive at a final concentration of 30% by weight of disodic terephthalate is found. The solution is brought to 70° C. and is extracted by 10% by weight of butanol. The extraction ended, the juice is passed over a column of activated charcoal which eliminates the remainder of the impurities and the bleached solution is then precipitated by addition of sulfuric acid up to a pH of 2.5-3 and the terephthalic acid recovered (yield: 1000 kg) is appropriately washed and dried.

Acid index 675
Ash 10 ppm
5% solution in dimethylformamide—color: alpha 10
Maximum H$_2$O 0.5%
Purity: 99.9%

Example 2

Same procedure as in example 1 but use of potassium (701 kg)—temperature 150° C.—yield 1003 kg of terephthalic acid.

Example 3

The piece of equipment is the same as in example 1.

1178 kg of support of X-ray films of glycol polyterephthalate are mixed with 700 kg of hydrated lime Ca(OH)$_2$; the temperature of the screw exchanger is 180° C.; the product is recovered in an amount of water corresponding to 100% dilution—The lime terephthalate is insoluble, it is filtered, washed and dried—it is then broken down into terephthalic acid as indicated in example 1.

Example 4

1200 kg of unwashed "bottle"—type polyester packages are ground and treated as in example 1—on the other hand, after dilution in water at a concentration of 20% of soda terephthalate, a filtration is performed that makes it possible to eliminate the insoluble products; the remainder of the operation is completed as in example 1.

The process is also applied successfully to the treatment of other polyterephthalates, and for example to the treatment of butylene glycol polyterephthalate.

I claim:

1. A process for the production of terephthalic acid or an alkali metal or alkaline-earth metal salt of terephthalic acid, comprising continuously reacting a polyol polyterephthalate with an alkali metal or alkaline-earth metal hydroxide, at 130°-190° C., at approximately atmospheric pressure, in the absence of water or in the presence of a maximum amount by weight of water equal to that of the alkali metal or alkaline-earth metal hydroxide, the proportion of alkali metal or alkaline earth metal hydroxide being 50 to 300% of the stoichiomatic amount necessary to produce entirely salified terephthalate, and optionally acidifying the salified terephthalate to produce terephthalic acid.

2. A process according to claim 1, wherein the reaction is performed with a proportion of hydroxide of 50 to 150% of the stoichiometric amount.

3. A process according to claim 1, wherein the operation is performed at 140°-180° C.

4. Process according to claim 1, wherein the proportion of hydroxide is approximately equal to the stoichiometric proportion.

5. Process according to claim 1, wherein the hydroxide is an alkali metal hydroxide and wherein, after the reaction, sufficient water is added to dissolve the alkaline metal terephthalate formed, before optional acidification.

6. A process according to claim 1, wherein the aqueous solution of alkaline metal terephthalate is subjected to an extraction by an alcohol of C3 to C8, preferably C4 to C8, in particular n-butanol.

7. A process according claim 1, wherein the polyol is separated from the aqueous solution of alkaline metal terephthalate by salting out with a compound which increases the ionic force of the solution.

8. A process according to claim 1, wherein the process is conducted continuously.

9. A terephthalic acid obtained by the process of claim 1.

10. In a process for the production of a polyol polyterephthalate, comprising polymerizing recycled terephthalic acid or a salt thereof, the improvement wherein the recycled terephthalic acid or salt is one produced according to claim 1.

11. A process for the recovery of terephthalic acid or a salt thereof, from polymeric materials, comprising continuously reacting a polyol polyterephthalate with an alkali metal hydroxide or alkaline earth metal hydroxide, at atmospheric pressure, in the absence of water or in the presence of a maximum amount by weight of water equal to that of the alkali metal or alkaline-earth metal hydroxide, so as to produce a solution of depolymwerized, salified terephthalate; and recovering said depolymerized, salified terephthalate, or optionally acidifying said depolymerized, salified terephthalate to produce terephthalic acid, and recovering said acid.

12. A process according to claim 11, wherein the polyol polyterephthalate contains additional polymers which are non-reactive with said alkali metal or alkaline-earth metal hydroxide, said process further comprising removing said non-reactive polymers from said solution of depolymerized, salified terephthalate by filtration.

13. A process according to claim 12, wherein the non-reactive polymer is polyethylene.

14. A process according to claim 11, wherein the process is conducted continuously.

* * * * *